(12) United States Patent
Tantaoui Elaraqi et al.

(10) Patent No.: US 9,757,331 B2
(45) Date of Patent: Sep. 12, 2017

(54) STABILIZED ACTIVE COMPOUND

(75) Inventors: Khadija Tantaoui Elaraqi, Liège (BE); Guy Broze, Grace-Hollogne (BE); Audrey Leruite, Herve (BE)

(73) Assignee: PRAYON SA, Engis (BE)

( * ) Notice: Subject to any disclaimer, the term of this patent is extended or adjusted under 35 U.S.C. 154(b) by 197 days.

(21) Appl. No.: 13/701,054

(22) PCT Filed: Jun. 24, 2011

(86) PCT No.: PCT/EP2011/060618
§ 371 (c)(1),
(2), (4) Date: Jan. 2, 2013

(87) PCT Pub. No.: WO2011/161236
PCT Pub. Date: Dec. 29, 2011

(65) Prior Publication Data
US 2013/0095150 A1    Apr. 18, 2013

(30) Foreign Application Priority Data

Jun. 24, 2010    (WO) .................. PCT/EP2010/059014

(51) Int. Cl.

| A61K 9/00 | (2006.01) |
|---|---|
| A61K 9/14 | (2006.01) |
| A61K 31/593 | (2006.01) |
| A23K 40/00 | (2016.01) |
| A23K 20/174 | (2016.01) |
| A23K 20/158 | (2016.01) |
| A23K 20/24 | (2016.01) |
| A23K 20/26 | (2016.01) |
| A23L 33/155 | (2016.01) |

(52) U.S. Cl.
CPC .......... *A61K 9/0087* (2013.01); *A23K 20/158* (2016.05); *A23K 20/174* (2016.05); *A23K 20/24* (2016.05); *A23K 20/26* (2016.05); *A23K 40/00* (2016.05); *A23L 33/155* (2016.08); *A61K 9/143* (2013.01); *A61K 9/145* (2013.01); *A61K 31/593* (2013.01); *A23V 2002/00* (2013.01)

(58) Field of Classification Search
None
See application file for complete search history.

(56) References Cited

U.S. PATENT DOCUMENTS

| 4,389,419 A | 6/1983 | Lim et al. |
|---|---|---|
| 5,820,903 A | 10/1998 | Fleury et al. |
| 6,569,463 B2 * | 5/2003 | Patel et al. .................... 424/497 |
| 6,790,462 B2 † | 9/2004 | Hendricks |
| 2003/0170324 A1 | 9/2003 | Tritsch et al. |
| 2006/0008533 A1 | 1/2006 | Habich et al. |
| 2009/0004308 A1 * | 1/2009 | Frehner et al. .............. 424/756 |
| 2010/0204204 A1 * | 8/2010 | Zaworotko ............... A23L 1/30 514/212.03 |

FOREIGN PATENT DOCUMENTS

| DE | 19710054 A1 | 9/1998 |
|---|---|---|
| GB | 405791 | 2/1934 |
| WO | 9840085 A1 | 9/1998 |
| WO | 03059358 A1 | 7/2003 |
| WO | WO2008063910 | * 5/2008 |

OTHER PUBLICATIONS

Ramadan, Mohamed. "Nutritional value, functional properties and nutraceutical applications of black cumin (*Nigella sativa* L.): an overview", 2007, International Journal of Food Science and Technology, vol. 42, pp. 1208-1218.*
International Search Report for related Application PCT/EP2011/060618 mailed Sep. 30, 2011.
http://www.fujicalin.com/library/application data.php.†

* cited by examiner
† cited by third party

*Primary Examiner* — Robert A Wax
*Assistant Examiner* — Randeep Singh
(74) *Attorney, Agent, or Firm* — Norris McLaughlin & Marcus P.A.

(57) ABSTRACT

Stable solid compositions have a first carrier and an adsorbate having at least one active component, such as, a vitamin D derivative and a hydrophobic stabilizer thereof, wherein the first carrier is a calcium phosphate or derivatives thereof having a solubility in water lower than 0.1 wt % at room temperature.

16 Claims, 2 Drawing Sheets

STABILIZED ACTIVE COMPOUND

This is a 371 of PCT/EP2011/060618 filed 24 Jun. 2011 (international filing date), and claims the priority of PCT/EP2010/059014 filed 24 Jun. 2010.

TECHNICAL FIELD

The present invention relates generally to the field of solid compositions comprising an adsorbate adsorbed onto a carrier. In particular, the present invention relates to compositions comprising one or more components adsorbed on a carrier and suitable for human or animal nutrition and/or health.

DESCRIPTION OF RELATED ART

Active compound-comprising preparations are widely used for human and animal foods, cosmetics or pharmaceutical compositions. Active compounds can be vitamins, additional nutrients, perfume oils, enzymes, or proteins.

Usually, such active compounds are dissolved or dispersed in a liquid solvent and the thus prepared solution is coated on particulate materials or encapsulated on a matrix in order to favor their incorporation in food, or their bioassimilation. All preparations share the problem of providing the respective active compound in an industrially handleable formulation. Prior art discloses various processes to prepare composition containing active compounds.

U.S. Pat. No. 4,389,419 discloses a process for encapsulating oils and oil-soluble substances in microcapsules. First, an emulsion is formed consisting of a continuous phase comprising an aqueous solution of an alkali metal alginate and alcohol-insoluble filler, and an oleophilic substance. US 2003/0170324 discloses an oil composition containing ingredients dissolved in an oil. A feed premix composition is also disclosed and comprises a microencapsulated oil and at least one nutritional additive.

U.S. Pat. No. 5,820,903 discloses nutritionally improved yogurt products including a calcium phosphate salt. The calcium content in the product is increased by addition of the calcium phosphate salt and ranges from 500 to 1500 mg per 170 g of yogurt.

WO98/40085 discloses a preparation containing an active component (e.g. vitamin $D_3$) and tricalcium phosphate. Vitamins such as vitamin D or metabolites thereof have received great interest. Indeed, vitamin D is known to have a major impact for controlling bone metabolism, immune system, neuro-degenerative diseases. Generally, the term "vitamin D" refers to vitamin $D_2$ and vitamin $D_3$ and derivatives thereof. Humans can only produce $D_3$ vitamins or calciferols by the action of ultraviolet rays from sunlight on the skin. Vitamin $D_3$ that is produced in the skin binds to the so-called vitamin D-binding protein which transports it into the liver where it is converted into 25-hydroxyvitamin $D_3$ by 25-hydroxylation. Preparations containing vitamin D ingredients have been prepared in the past. Vitamin D, however, most vitamins, and many active compounds in general have a limited life time, usually shorter than the food or pharmaceutical preparations they are incorporated into. In addition, it is difficult to homogeneously disperse small amounts of active compound onto a carrier.

US2006/0008533 discloses the stabilization of active compounds by mixing them with a stabilizer and a coating material. The resulting preparation is adsorbed onto a silica carrier. GB 405,791 discloses a process for the manufacture of food accessories for cattle which consists in absorbing cod-liver oil on calcium carbonate.

Preparations known in the art, however, give unsatisfactory results in term of stability in time of the active components which can be oxidized or isomerized in a few days. Therefore, there is a need for preparations suitable for easily and homogeneously adding even small quantities of active compounds to a composition such as food or pharmaceutical preparations, and further enhancing the stability of said active compounds in a simple and economic way. The present invention aims at providing a composition fulfilling the above need and overcoming the above-discussed drawbacks of the prior art.

SUMMARY OF THE INVENTION

It is an object of the present invention to provide a composition wherein an active component is stabilized. It is an object of the present invention to provide a stable composition which prevents oxidation of the active component. It is another object of the invention to provide a composition whereby an efficient amount of the active component is delivered homogeneously. It is another object of the invention to enhance the dispersion of an active component within a composition. In particular, it is another object of the present invention to provide a composition which is calcium-enriched. In particular, it is another object of the present invention to provide a composition stabilizing vitamin D derivatives.

According to a first aspect, the present invention provides a stable solid composition comprising a first carrier and an adsorbate adsorbed thereon, said adsorbate comprising at least one active component and a hydrophobic stabilizer thereof, wherein said first carrier is a calcium phosphate or derivatives thereof having a solubility in water lower than 0.1 wt % at room temperature. Said hydrophobic stabilizer enhances the dispersion of an active component within a composition and, if properly selected, may contribute to the enhancement of the stability of the active component, e.g., by preventing oxidation thereof. Said first calcium phosphate based carrier provides, together with the adsorbate, an unexpected enhancement of the stability of the active compound. Said carrier and/or said hydrophobic stabilizer may enhance the stability of the active component.

According to a second aspect, the invention provides a process for the preparation of a stable solid composition comprising the steps of:
 dispersing at least one active component into a hydrophobic stabilizer to form an adsorbate,
 contacting said adsorbate with a first carrier, and adsorbing the former onto the first carrier, said first carrier being calcium phosphate or derivatives thereof having a solubility in water lower than 0.1 wt % at room temperature,
 homogenising the composition obtained in the previous step, to form a stable solid composition.

According to a third aspect, the invention provides the use of the composition according to the present invention as food ingredient in human or animal food.

According to a fourth aspect, the invention provides the use of the composition according to the present invention in a pharmaceutical preparation.

DETAILED DESCRIPTION OF THE INVENTION

Figure 1:
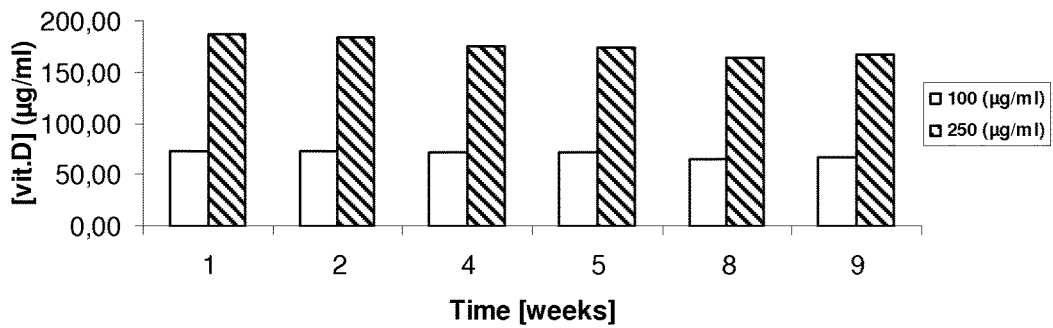
FIG. 1 represents the evolution over a period of nine weeks of the effective amount of vitamin $D_3$ (expressed in µg/ml) recovered from a composition according to the present invention for various concentrations in active component.

The present invention provides a stable calcium enriched composition comprising active component(s) that enhances the stability in time of said active component(s). Hence, the present invention relates to a stable solid composition comprising a first carrier and an adsorbate, adsorbed thereon, said adsorbate comprising at least one active component and a hydrophobic stabilizer thereof. According to the present invention, said carrier is calcium phosphate or derivatives thereof having a solubility in water lower than 0.1 wt % at room temperature. Room temperature is considered to be 25° C. Said first carrier enhances the stability of the active component as depicted in the examples below. The stability provided by calcium phosphate, having a solubility in water lower than 0.1 wt % at room temperature, was unexpected with respect to the low or moderate stabilizing effect of other known carriers such as calcium carbonate or silica.

The term calcium phosphate refers to minerals containing calcium ions ($Ca^{2+}$) together with orthophosphates ($PO_4^{3-}$), metaphosphates ($P_3O_9^{3-}$) or pyrophosphates ($P_2O_7^{4-}$) and occasionally hydrogen or hydroxide ions. In a preferred embodiment, calcium phosphate may be dicalcium phosphate or tricalcium phosphate. The "di-" and "tri-" prefixes denote that two or three of the hydrogen atoms in phosphoric acid respectively are replaced by calcium atom.

In a preferred embodiment, calcium phosphate may be tricalcium phosphate. The term "tricalcium phosphate" or "TCP" refers to tribasic calcium phosphate $Ca_3(PO_4)_2$ and also encompasses apatite, calcium orthophosphate, tertiary calcium phosphate, carbonate-apatite, or mixture thereof. The common mineral apatite has formula $Ca_5(PO_4)_3X$, where X is F, Cl, OH, $CO_3$ or mixture thereof. Hydroxyapatite refers to a compound of formula $Ca_5(PO_4)_3X$, wherein X is hydroxide. Fluorapatite refers to a compound of formula $Ca_5(PO_4)_3X$, wherein X is fluoride. Carbonate-apatite refers to a compound of formula $Ca_5(PO_4)_3X$ wherein X is $(CO_3)_{1/2}$.

In a preferred embodiment, calcium phosphate may be selected from the group consisting of tribasic calcium phosphate, hydroxyapatite, fluorapatite, and carbonate-apatite or mixture thereof.

Said first carrier may be calcium phosphate having Ca/P molar ratio ranging from 0.95 to 2.0. The ratio Ca/P of calcium phosphate may influence the stability of the active component. The choice of a particular calcium phosphate may depend on the active component to be adsorbed thereon. Preferably, the molar ratio Ca/P of calcium phosphate may range from 1.5 to 2.0. More preferably, the molar ratio Ca/P of calcium phosphate may range from 1.5 to 1.75, most preferably, the molar ratio Ca/P may range from 1.6 to 1.7.

In a preferred embodiment, calcium phosphate may have a water content lower than 3.0%, preferably lower than 1.0%, more preferably lower than 0.5%.

As mentioned above, the composition of the invention comprises a first carrier and an adsorbate. The term "adsorbate" as used in the present invention refers to a substance or a composition that is adsorbed or is to be adsorbed on a surface or a carrier. In a preferred embodiment, the weight ratio between the first carrier and the adsorbate ranges from 200:1 to 2:1, preferably from 100:1 to 4:1.

The adsorbate according to the present invention contains a hydrophobic stabilizer and at least one active component. Hence, said adsorbate may comprise more than one active component and thus the composition of the present invention may comprise more than one active component. The term "a hydrophobic stabilizer" refers to one hydrophobic stabilizer or a mixture comprising more than one hydrophobic stabilizer as described hereunder.

The weight ratio between said at least one active component and said hydrophobic stabilizer in the adsorbate may range from 1:2 to 1:100, preferably from 1:10 to 1:40.

Suitable active component may be any active component which is suitable for human or animal consumption or health. The active component may be oil-soluble, and is preferably soluble in the hydrophobic stabilizer. Said at least one active component may be selected from the group consisting of vitamins, perfume oils, flavours, carotenoids, xanthophylls, antioxidants, unsaturated fatty acids, oil-soluble enzymes and oil-soluble proteins. Active components are considered to be oil-soluble as soon as their solubility in water at room temperature (25° C.) falls below 1 wt %.

The term "perfume oils" refers to natural or synthetic fragrances or mixture thereof. Natural fragrances may be extracts of blossoms (lily, lavender, roses, jasmine, neroli, ylang-ylang), stems and leaves (geranium, patchouli, petitgrain), fruits (aniseed, coriander, cumene, juniper), fruit rinds (bergamot, lemons, oranges), roots (mace, angelica, celeriac, cardamon, costus, iris, calmus), woods (pinewood, sandalwood, guaiac wood, cedarwood, rosewood), herbs and grasses (tarragon, lemongrass, sage, thyme), needles and twigs (spruce, fir, pine, mountain pine), resins and balsams (galbanum, elemi, benzoin, myrrh, olibanum, opoponax). In addition, animal raw materials are used, for example civet and Castoreum. Typical synthetic fragrance compounds may be products of the types esters, ethers, aldehydes, ketones, alcohols and hydrocarbons. Fragrance compounds of the ester type may be, for example, benzyl acetate, phenoxyethyl isobutyrate, p-tert-butylcyclohexyl acetate, linalyl acetate, dimethylbenzylcarbonyl acetate, phenylethyl acetate, linalyl benzoate, benzyl formate, ethylmethylphenyl glycinate, allyl cyclohexylpropionate, styrallyl propionate and benzyl salicylate. The ethers may include, for example, benzyl ethyl ether, the aldehydes, for example, the linear alkanals containing from 8 to 18 carbons, citral, citronellal, citronellyloxyacetaldehyde, cyclamen aldehyde, hydroxycitronellal, lilial and bourgeonal, the ketones, for example, the ionones, [alpha]-isomethylions and methyl cedryl ketone, whose alcohols include anethole, citronellol, eugenol, isoeugenol, geraniol, linalool, phenylethyl alcohol and terpireol; the hydrocarbons principally may include the terpenes and balsams. However, preference is given to using mixtures of various fragrances which together generate an appealing aroma note. Essential oils of less volatility which are generally used as flavor components are also suitable as perfume oils, for example sage oil, camomile oil, clove oil, lemon balm oil, mint oil, cinnamon leaf oil, lime blossom oil, juniper berry oil, vetiver oil, olibanum oil, galbanum oil, labolanum oil and lavandin oil. Preferably, use is made, alone or in mixtures, of bergamot oil, dihydromyrcenol, lilial, lyral, citronellol, phenylethyl alcohol, [alpha]-hexyl-cinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, b-damascone, geranium oil bourbon, cyclohexyl salicylate, vertofix coeur, iso-E-super, Fixolide NP, Evernyl, iraldein gamma, phenylacetic acid, geranyl acetate, benzyl acetate, rose oxide, romilat, irotyl and Floramat.

The term "carotenoids and xanthophylls" refers but is not limited to lycopene, [beta]-carotene, [alpha]-carotene, astaxanthin, astaxanthin esters, canthaxanthin, citranaxanthin, beta-Apo-8'-carotenic acid ethyl ester, beta-Apo-8'-carotenal, lutein and lutein esters, zeaxanthin and zeaxanthin esters, [beta]-cryptoxanthin and [beta]-cryptoxanthin esters, capsanthin and capsanthin esters, capsorubin and capsorubin esters, bixin, bixin esters and derivatives thereof, norbixin, norbixin esters and derivatives thereof, crocetin, crocetin esters and derivatives thereof, or mixtures thereof.

The term "unsaturated fatty acids" refers to, but is not limited to, compounds of general formula $RCO_2H$ wherein R is $C_{3-22}$ linear, unbranched hydrocarbyl radical containing at least one double bond. The term "$C_{3-22}$ hydrocarbyl radical" means that the hydrocarbyl radical has from 3 to 22 carbon atoms. The term "unsaturated fatty acids" encompasses the salts and esters of the respective acids, in particular the alkali metal salts and alkaline earth metal salts and the $C_{1-4}$ alkyl esters. The term "alkyl esters" refers to hydrocarbyl radical having from 1 to 4 carbon atoms. For example, $C_{1-4}$ alkyl esters may be methyl, ethyl, n-propyl, isopropyl, n-butyl, isobutyl, sec-butyl, and tert-butyl. The unsaturated fatty acids contain one, two, three, four, five or six double bonds in the acyl radical. Particularly suitable unsaturated fatty acids may be [omega]-3, [omega]-6 and [omega]-9 fatty acids. Examples of the [omega]-3 fatty acids are [alpha]-linolenic acid, oleic acid, palmitoleic acid and myristoleic acid, of the [omega]-6 fatty acids, linoleic acid, [gamma]-linolenic acid and arachidonic acid, and of the [omega]-9 fatty acids, oleic acid, erucic acid and nervonic acid.

The term "flavour" refers to natural and synthetic flavouring substances. Flavour may be, but is not limited to, diacetyl, isoamyl acetate, benzaldehyde, cinnamic aldehyde, ethyl propionate, Methyl anthranilate, limonene, [[Ethyl-(E, Z)-2,4-decadienoate]], Allyl hexanoate, Ethyl maltol, Ethyl vanillin, Methyl salicylate.

The term "antioxidant" refers to compound able of slowing or preventing the oxidation of other molecules.

The term "oil-soluble enzymes or proteins" refers to natural or synthetic enzymes or proteins being soluble in oil or to enzymes or proteins being substituted to be soluble in oil. The term encompasses oil-soluble coenzyme and cofactor.

The term "vitamins" refers to vitamins such as vitamin A, vitamin D, vitamin E, phylloquinone (vitamin $K_1$) and menaquinone (vitamin $K_2$). Vitamin A refers but is not limited to, all retinoids which qualitatively exhibit the biological activity of all-trans retinol and also its esters, such as vitamin A acetate, vitamin A propionate, vitamin A palmitate and other esters or derivatives of vitamin A. The term "vitamin E" refers but is not limited to, all derivatives of tocol and tocotrienol which quantitatively exhibit the biological activity of α-tocopherol. These include α-, β, and γ tocopherol and also α-, β, and γ tocotrienol and corresponding diastereoisomers. The term "vitamin D" refers but is not limited to vitamin $D_2$ (ergocalciferol), vitamin $D_3$ (cholecalciferol) and derivatives thereof, and metabolites thereof.

In a preferred embodiment, said at least one active component may be selected from the group consisting of vitamins, perfume oils, flavours, carotenoids, xanthophylls, antioxidants, and unsaturated fatty acids. Numerous combination of the active component can be foreseen. The invention was experimentally evaluated with respect to vitamin D derivatives, such as vitamin $D_3$, but is not limited to them.

In a more preferred embodiment, said at least one active component may comprise at least a vitamin. Preferably, said at least one active component may comprise at least a vitamin D derivative. More preferably, said at least one active component may comprise at least vitamin $D_3$ or derivatives thereof. Alternatively, said at least one active component may be vitamin $D_3$ or derivatives thereof.

The hydrophobic stabilizer suitable for the present invention may comprise one or more $C_{3-22}$ fatty acids or ester or glyceride derivatives thereof, or mixture thereof. The term "$C_{3-22}$ fatty acid" means an alkyl having from 3 to 22 carbon atoms. The ester derivatives may be an alkyl radical having from 1 to 4 carbon atoms. The term glyceride encompasses tri-, di-, mono-glyceride and phosphoacylglycerol. Said hydrophobic stabilizer may stabilize said at least one active component. For example, the hydrophobic stabilizer may prevent oxidation of at least one active component. The hydrophobic stabilizer is a liquid compound or composition suitable for stabilizing at least one active component. Preferably, the hydrophobic stabilizer may be an oil.

In a preferred embodiment, said hydrophobic stabilizer may further comprise one or more antioxidant(s). The antioxidant capacity of the hydrophobic stabilizer may be expressed in terms of degree of polyphenols or of tocopherol in said hydrophobic stabilizer. For example, the hydrophobic stabilizer may have an antioxidant content expressed as a degree of polyphenols in the hydrophobic stabilizer of at least 1 mg gallic acid per kg of hydrophobic stabilizer; preferably, the antioxidant content may be at least 10 mg gallic acid per kg of hydrophobic stabilizer. The degree of polyphenols was determined according the method of Folin-Ciocalteau commonly used in the art. The antioxidant content of the hydrophobic stabilizer can further improve the stability of the composition.

In a preferred embodiment, said hydrophobic stabilizer may be an oil. Said oil may comprise at least 20 wt % of $C_{10-22}$ fatty acids or ester or glyceride derivatives thereof. The hydrophobic stabilizer may be an oil comprising unsaturated fatty acids or ester or glyceride derivatives thereof. The term "unsaturated" means that fatty acids may have one or more double or triple carbon-carbon bond(s) along the hydrocarbon chain. Therefore, the term "unsaturated fatty acids or ester or glyceride derivatives thereof" encompasses polyunsaturated fatty acids or ester or glyceride derivatives thereof. Preferably, said hydrophobic stabilizer may be an oil comprising at least 55 wt % of unsaturated fatty acids or ester or glyceride derivatives thereof. The composition of the hydrophobic stabilizer may further improve the stability of the active component.

The hydrophobic stabilizer may be for example, but is not limited to, safflower oil, grape seed oil, poppyseed oil, sunflower oil, hemp oil, *Nigella sativa* oil, corn oil, wheat germ oil, cottonseed oil, soybean oil, walnut oil, olive oil, Argan oil, Soya oil, canola oil or sesame oil.

In particular, the hydrophobic stabilizer may be *Nigella sativa* oil. This latter is an oil comprising at least 40 wt % of linoleic acid and at least 15 wt % oleic acid or ester or glyceride derivatives thereof. *Nigella sativa* oil has an antioxidant content of at least 230 mg gallic acid per kg of oil.

According to a second aspect, the present invention provides a process for the preparation of a stable solid composition comprising the steps of:
  dispersing at least one active component into a hydrophobic stabilizer to form an adsorbate,
  contacting said adsorbate with a first carrier, and adsorbing the former onto the first carrier, said first carrier being calcium phosphate or derivatives thereof having a solubility in water lower than 0.1 wt % at room temperature,
  homogenising the composition obtained in the previous step, to form a stable solid composition.

The term "homogenising" means mixing until homogeneity. Preferably, said first carrier may be dicalcium phosphate or tricalcium phosphate. More preferably, the first carrier may be tricalcium phosphate as defined above. Most preferably, said first carrier may be selected from the group consisting of tribasic calcium phosphate, hydroxyapatite, fluorapatite and carbonate-apatite or mixture thereof.

In another preferred embodiment, said first carrier may be calcium phosphate having Ca/P molar ratio ranging from 0.95 to 2.0. Preferably, the molar ratio Ca/P of calcium phosphate may range from 1.5 to 2.0. More preferably, the molar ratio Ca/P of calcium phosphate may range from 1.5 to 1.75, most preferably the molar ratio Ca/P may range from 1.6 to 1.7.

In another preferred embodiment, calcium phosphate may have water content lower than 3.0%, preferably lower than 1.0%, more preferably lower than 0.5%.

In the process of the invention, at least one active component is dispersed in a hydrophobic stabilizer to form an adsorbate according to the present invention. Alternatively, one or more active component may be dispersed in one or more hydrophobic stabilizer to form an adsorbate according to the present invention. More than one active component may be provided in the process and dispersed into said hydrophobic stabilizer simultaneously or not. In the process of the invention, the weight ratio between said at least one active component and said hydrophobic stabilizer in the adsorbate may range from 1:2 to 1:100, preferably, from 1:10 to 1:40.

Suitable active component used in the process of the invention may be active components which are suitable for human or animal consumption or health. The active component may be oil-soluble, and is preferably soluble in the hydrophobic stabilizer. Said active component may be selected from the group consisting of vitamins, perfume oils, flavours, carotenoids, xanthophylls, antioxidants, unsaturated fatty acids, oil-soluble enzymes and oil-soluble proteins, as defined above. Said active components are considered to be oil-soluble as soon as their solubility in water at room temperature (25° C.) falls below 1 wt %. Preferably, said at least one active component may be selected from the group consisting of vitamins, perfume oils, flavours, carotenoids, xanthophylls, antioxidants, and unsaturated fatty acids. In a preferred embodiment, said at least one active component, used in the present process, is defined above with respect to the composition of the present invention.

In the process of the present invention, said hydrophobic stabilizer may comprise one or more $C_{3-22}$ fatty acids or ester or glyceride derivatives thereof, or mixture thereof. The ester derivatives may be an alkyl having from 1 to 4 carbon atoms. The term glyceride encompasses tri-, di-, mono-glyceride and phosphoacylglycerol. In a preferred embodiment, said hydrophobic stabilizer may further comprise one or more antioxidant(s). Preferably, said hydrophobic stabilizer may be an oil comprising at least 20 wt % of $C_{10-22}$ fatty acids or ester or glyceride derivatives thereof. The hydrophobic stabilizer may be an oil comprising unsaturated fatty acids or ester or glyceride derivatives thereof. In a preferred embodiment, the hydrophobic stabilizer may be an oil comprising at least 55 wt % of unsaturated fatty acids or ester or glyceride derivatives thereof.

Hence, the hydrophobic stabilizer may be for example, but is not limited to, safflower oil, grape seed oil, poppyseed oil, sunflower oil, hemp oil, *Nigella sativa* oil, corn oil, wheat germ oil, cottonseed oil, soybean oil, walnut oil, olive oil, Argan oil, Soya oil, canola oil or sesame oil. Preferably, the hydrophobic stabilizer may be *Nigella sativa* oil.

In a preferred embodiment, the process may further comprise the step of homogenizing the adsorbate. The homogenization of the adsorbate enhances the dispersion of the at least one active component in a hydrophobic stabilizer.

When the adsorbate is formed, it is contacted with and adsorbed on a first carrier as defined above. The weight ratio between the carrier and the adsorbate may range from 200:1 to 2:1. Preferably, the weight ratio between the carrier and the adsorbate may range from 100:1 to 4:1. Homogenization of the composition obtained after dispersion of the adsorbate on the carrier affords a stable and solid composition according to the present invention.

According to a third aspect, the invention provides the use of the composition according to the present invention as food ingredient. Hence, said composition may be used for example in dairy products, beverages such as fruit juice, cereals, and the like. The composition of the present invention may be used as food ingredient in human or animal foods. Therefore, the invention provides human or animal food composition comprising the composition of the present invention. As mentioned above, said food may be dairy products, beverages, cereals and the like. Dairy products may be foods produced from cow's, buffalo's, sheep's, goat's, camel's, yak's or horse's milk. Dairy products may be for example milk, butter, cheese, yogurt, ice cream or gelato.

According to another aspect of the invention, the composition according to the present invention may be used in a pharmaceutical preparation. Such pharmaceutical preparation may further comprise an excipient or a second carrier, and any additional component well known in the art which is traditionally added to such preparations. Examples of excipients are, but are not limited to, mannitol, hydroxypropylcellulose, lactose, polyvinylpyrrolidone, polyvinyl alcohol, gelatin, starch, crystalline cellulose, hydroxypropylmethylcellulose, ethylcellulose, carboxymethylcellulose, dextrin, lactose, sorbitol, sucrose, magnesium silicate hydrate, kaolin, precipitated calcium carbonate, sodium chlorine, titanium oxide, gum arabic and/or xanthan gum. Said second carrier may be a organic or inorganic substances which are suitable for oral administration and do not react with the compounds, for example, gelatin, soy lecithin, carbohydrates such as lactose, mannitol or starch, magnesium stearate, talc, cellulose. For oral administration, tablets, coated tablets, capsules, suspension or granules or powders, dispensed in sachets for use in suspension, are used.

Said pharmaceutical preparation may be suitable for the treatment or prophylaxis of osteoporosis, or calcium deficiency states. Said pharmaceutical preparation may be used for the manufacture of a medicament for the treatment or prophylaxis of osteoporosis, or calcium deficiency states.

In a preferred embodiment, the composition used in said pharmaceutical preparation may comprise tricalcium phosphate as defined above and an adsorbate comprising at least one vitamin D derivatives and Nigella sativa oil. In particular, pharmaceutical preparation may comprise tricalcium phosphate and an adsorbate comprising vitamin $D_3$ or derivatives thereof and Nigella sativa oil. Hence, said pharmaceutical preparation may be suitable for the treatment or prophylaxis of osteoporosis, or calcium and/or vitamin D deficiency states. Said pharmaceutical preparation may be used for the manufacture of a medicament for the treatment or prophylaxis of osteoporosis, or vitamin D and/or calcium deficiency states. In a preferred embodiment, said vitamin $D_3$ may be in an active form. Said active form of vitamin $D_3$ may be but is not limited to, 1α-hydroxycholecalciferol, 1α,25-dihydroxycholecalciferol, 1α,24-dihydroxycholecalciferol, 1α,24,25-trihydroxycholecalciferol, 1α-hydroxy-24-oxocholecalciferol, 1α,25-dihydroxy-24-oxo-cholecalciferol, 1α,25-dihydroxy-cholecalciferol-26,23-lacton, 1α,25-dihydroxy-cholecalciferol-26,23-peroxylacton or 26,26,26,27,27,27-hexafluoro-1α,25-dihydroxycholecalciferol, 25-Hydroxycholecalciferol, 24-hydroxycholecalciferol, 24-oxocholecalciferol, 24,25-dihydroxycholecalciferol, 25-hydroxy-24-oxo-cholecalciferol, 25-hydroxycholecalciferol-26,23-lacton or 25-Hydroxycholecalciferol-26,23-peroxylacton.

In another aspect of the invention, an adsorbate comprising an active compound with enhanced stability in time is provided. Said adsorbate comprises at least one active component and Nigella sativa oil. Said at least one active component may be any of those described above with respect to the composition of the present invention. Said at least one active component may be selected from the group consisting of vitamins, perfume oils, flavours, carotenoids, xanthophylls, antioxidants, and unsaturated fatty acids. In a more preferred embodiment, said at least one active component may comprise at least a vitamin. Preferably, said at least one active component may comprise at least a vitamin D derivative. More preferably, said at least one active component may comprise at least vitamin $D_3$ or derivatives thereof. In particular, said adsorbate may contain Nigella sativa oil and vitamin $D_3$ derivatives.

EXAMPLES

Adsorbate and Composition Preparation Procedure

Vitamin $D_3$ or cholecalciferol is known to be easily oxidized or isomerised in few hours at room temperature and/or light ambient conditions. Hence, vitamin $D_3$ was used as model compound to study the efficiency of the adsorbate and of the composition according to the present invention in stabilizing active components.

Vitamin $D_3$ was first dispersed on a predetermined amount of a hydrophobic stabilizer. The mixture was mixed under magnetic stirring for few minutes at room temperature. An adsorbate was then obtained. A defined amount of said adsorbate was then adsorbed on a first carrier and the reaction mixture obtained was homogenized to form the composition according to the invention. The assessment of vitamin $D_3$ stability within a composition or a adsorbate was performed by extraction thereof from the adsorbate or from the composition. Non limitative organic solvents used for extraction can be methanol, ethanol or acetonitrile. The extraction of vitamin $D_3$ may be enhanced depending on the solvent and extraction conditions used. An aliquot from the adsorbate or from the composition was sampled for each vitamin $D_3$ extraction. The amount of vitamin $D_3$ recovered was measured by HPLC. HPLC analysis were performed in following conditions: methanol was used as eluent, isocratic HPLC pump having a flow rate of 1 ml/min, DAD1 detector detecting at 254.4 nm and HPLC column (AGILENT Technology A-Series) having apolar stationary phase were used. A first aliquot was sampled 24 h after the preparation of the composition or of the adsorbate; this corresponds to t=0 in the following tables. Other aliquots were sampled after one, two, three weeks or several months.

Example 1

Composition of the Present Invention

The amount of vitamin $D_3$ recovered from a composition A according to the present invention was evaluated over four weeks. Said composition comprises hydroxyapatite (ratio Ca/P of 1.67 and water content 0.3%) as first carrier and an adsorbate comprising vitamin $D_3$ and Nigella sativa oil (20 wt % of adsorbate was added in the composition). The adsorbate comprises 100 µg/ml of vitamin $D_3$. The amount of vitamin $D_3$ extracted with methanol at t=0 was 72.5 µg/ml. Since, the amount of vitamin $D_3$ recovered depends on solvent used for the extraction, an arbitrary value R0 of 100 was assigned to the amount extracted at t=0. Normalized values, noted R, were then expressed compared to the initial value obtained at t=0.

The composition A according to the present invention was compared to the corresponding adsorbate B, i.e. without carrier. The adsorbate B comprises vitamin $D_3$ and Nigella sativa oil but no carrier. The concentration of vitamin $D_3$ in the adsorbate B was 100 µg/ml. After three weeks, a normalized value R3 of 99.4 was obtained with the composition A instead of a normalized value of 90.9 with the adsorbate B. Within the composition according to the present invention, vitamin $D_3$ remains stable over a period of at least four weeks. Hence, the carrier of the present composition enhances the stability of the active component. This would not have been expected by man skilled in the art.

Additional experiments were performed over nine weeks. FIG. 1 depict the amount (expressed in µg/ml) of vitamin $D_3$ recovered over nine weeks from a composition comprising hydroxyapatite (ratio Ca/P of 1.67 and water content 0.3%), and an adsorbate comprising Nigella sativa oil and vitamin $D_3$. The experiment was performed in presence of 100 µg/ml (hollow) and 250 µg/ml (hatching) of vitamin $D_3$ in the adsorbate. After nine weeks, 66.2 µg/ml and 166.7 µg/ml of vitamin $D_3$ were recovered respectively. This underlines the great capacity of the first carrier and/or the hydrophobic stabilizer to enhance stability of vitamin $D_3$.

Example 2

Influence of the Carrier

Figure 2:
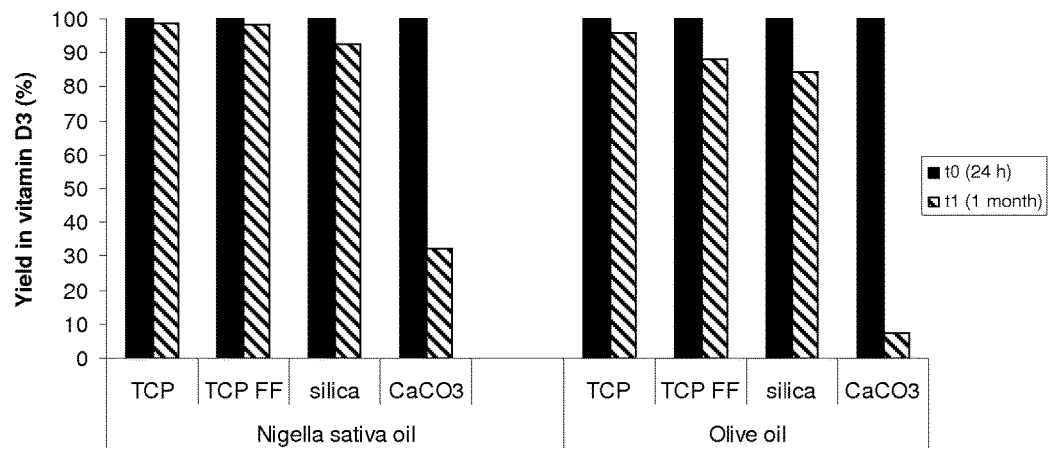
FIG. 2 represents the evolution over a period of one month of the percentage of vitamin $D_3$ (or yield in vitamin $D_3$) recovered from compositions comprising various carriers, and *Nigella sativa* oil or olive oil as hydrophobic stabilizer.

Comparative examples were performed with various carriers such as calcium phosphate (two different grades), silica or calcium carbonate. Tests were carried out with calcium phosphate having a water content of less than 0.3 wt %, noted as "TCP". Calcium phosphate having a water content of 2.31 wt % was also tested and noted as "TCP FF". FIG. 2 represents the evolution of vitamin $D_3$ recovered from compositions comprising vitamin $D_3$ and *Nigella sativa* oil or olive oil as hydrophobic stabilizer and four different carriers. Said carriers were TCP, TCP FF, silica or calcium carbonate ($CaCO_3$). The stability was assessed after one month (FIG. 2, hatching). These data show that calcium carbonate was not suitable to stabilize active component irrespective of the hydrophobic stabilizer. The yield of vitamin $D_3$ recovered after one month was 32.3% and 7.5% with *Nigella Sativa* oil and olive oil respectively. Said first carriers of the present invention, i.e. TCP and TCP FF show excellent results since the yield of vitamin $D_3$ recovered was higher than 98% in presence of *Nigella Sativa* oil. In contrast, with a silica carrier, the yield was around 92% in presence of *Nigella Sativa* oil. This was also confirmed with olive oil as hydrophobic stabilizer. Indeed, the yield of vitamin $D_3$ recovered with both TCP carriers, TCP and TCP FF, was higher than the one with silica, 96%, 88% and 84% respectively.

Figure 3:
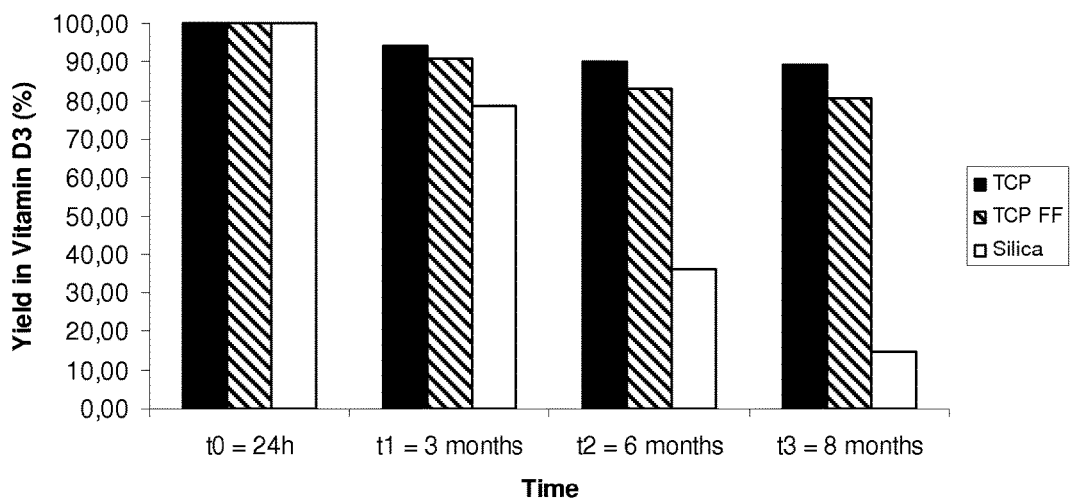
FIG. 3 represents the evolution over a period of time of eight months of the percentage of vitamin $D_3$ recovered from compositions comprising various carriers.

Based in these results, testing over a long period of time was performed with calcium phosphate, TCP and TCP FF, or silica as first carrier, and *Nigella sativa* oil as hydrophobic stabilizer. Aliquots were sampled at to (24 h), t1 (3 months), t2 (6 months) and t3 (8 months) to assess the stability of vitamin $D_3$. Results are represented in FIG. 3. The first carriers of the present invention, TCP (black rectangle) and TCP FF (hatched rectangle), show significant ability to stabilize vitamin $D_3$ over time compared to silica. The amount of vitamin $D_3$ in the composition remains higher than 80% with the composition of the present invention while it falls to only 15% with silica (white rectangle).

The examples above surprisingly highlight that compositions according to the present invention comprising an adsorbate, i.e. at least one active component and a hydrophobic stabilizer, adsorbed on a calcium phosphate carrier, having a solubility in water lower than 0.1 wt % at room temperature, stabilize the active component such as vitamin $D_3$ for at least eight months. Hence, an unexpected and surprising effect was obtained when using calcium phosphate, as previously defined, as first carrier in the composition.

Example 3

Influence of the Hydrophobic Stabilizer Composition

Example 3 reports the amount of vitamin $D_3$ recovered from an adsorbate comprising vitamin $D_3$ (active component), and linseed oil or *Nigella sativa* oil as hydrophobic stabilizer over three weeks. Table 1 summarizes the results. Initial concentration of vitamin $D_3$ in the adsorbate was 100 µg/ml. The control corresponds to an adsorbate without vitamin $D_3$. The amount of vitamin $D_3$ extracted at t=0 from the adsorbate comprising linseed oil was 59.8 µg/ml while the effective amount of vitamin $D_3$ extracted from the adsorbate comprising *Nigella sativa* oil was 75.2 µg/ml, both values were normalized at R0=100 in table 1. This experiment was performed in experimental conditions in which the adsorbate was in contact with ambient air to accelerate the oxidation process. After three weeks, a normalized value R3 of 90.9% was obtained when *Nigella sativa* oil was used while the normalized value was 26.6% when linseed oil was used. Hence, vitamin $D_3$ was moderately stabilized when dispersed in linseed oil compared to *Nigella sativa* oil.

TABLE 1 vitamin $D_3$ %-extracts in different compositions

|  | t = 0 | t = 1 week | t = 2 weeks | t = 3 weeks |
|---|---|---|---|---|
| *Nigella sativa* oil | 0 | | | |
| Vit D3 + Linseed oil | 100 | 44.1 | 32.3 | 26.6 |
| Vit D3 + *Nigella sativa* oil | 100 | 97.2 | 94.4 | 90.9 |

Figure 4:
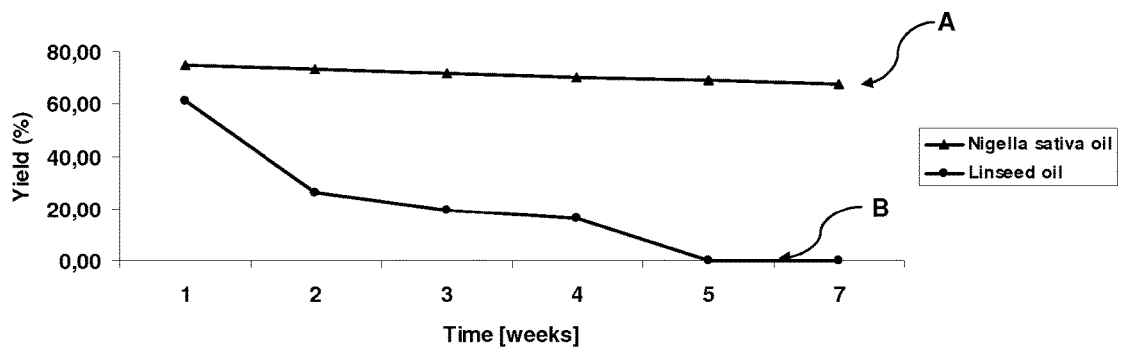
FIG. 4 represents the evolution over a period of seven weeks of the amount of vitamin $D_3$ recovered from an adsorbate comprising vitamin $D_3$ dispersed in *Nigella sativa* oil (curve A) and in linseed oil (curve B).

The yield of the effective amount of vitamin $D_3$ (expressed in %) recovered over seven weeks was showed on FIG. 4. Curve A represents the adsorbate comprising *Nigella sativa* oil while curve B represents the one with linseed oil. The effective amount of vitamin $D_3$ recovered (extraction with methanol) was higher than 65% after seven weeks (FIG. 4, curve A). When optimizing extraction conditions, more than 80% of vitamin $D_3$ was extracted. *Nigella sativa* oil was more efficient than linseed oil in stabilizing an active component such as vitamin $D_3$.

Example 3 shows that vitamin $D_3$ can be stabilized in presence of a hydrophobic stabilizer comprising one or more $C_{3-22}$ fatty acids. Without to be bound by the theory, these tests suggest that the hydrophobic stabilizer composition may influence the stability of the active component. Unsaturated fatty acid and/or linoleic acid contents may also enhance stabilization of active component such as vitamin $D_3$.

Example 4

Influence of the Antioxidant Content in the Hydrophobic Stabilizer

It was also found that the antioxidant content of the hydrophobic stabilizer may also influence the stability of the active ingredient.

Figure 5:
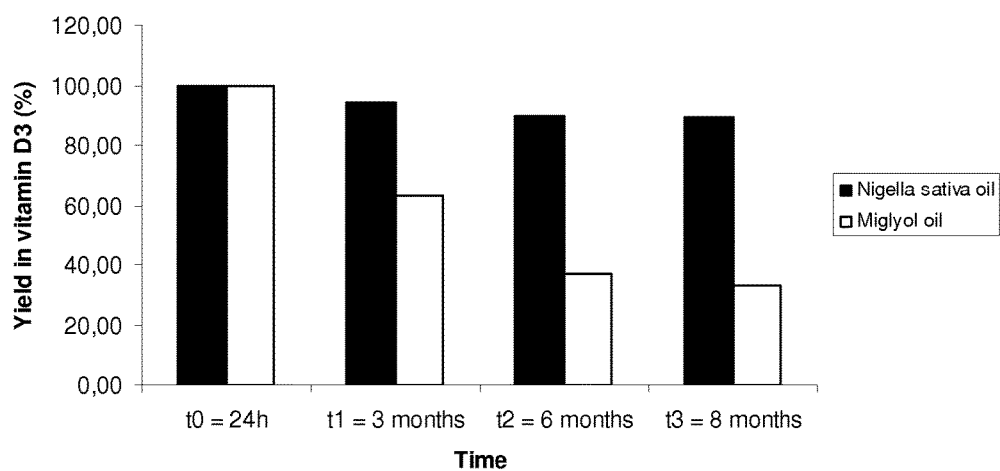
FIG. 5 represents the evolution over a period of time of eight months of the percentage of vitamin $D_3$ recovered from compositions comprising neutral oil and antioxidants-comprising oil.

A comparative example was performed to compare neutral oil, i.e. miglyol oil versus antioxidant-enriched oil such as *Nigella sativa* oil. The antioxidant capacity of a hydrophobic stabilizer can be expressed, for example, as a degree in polyphenols in said hydrophobic stabilizer. FIG. 5 represents the evolution of vitamin $D_3$ recovered from compositions comprising calcium phosphate as carrier and either miglyol (white rectangle) or *Nigella sativa* oil (black rectangle) as hydrophobic stabilizer. Miglyol oil is known to be free of antioxidant while *Nigella sativa* oil is antioxidant-enriched with an antioxidant content of at least 230 mg gallic acid per kg of oil. Over eight months, the amount of vitamin $D_3$ recovered remains quite stable with *Nigella sativa* oil (e.g. 89%) while in presence of miglyol the amount strongly decreased until 33%.

Figure 6:
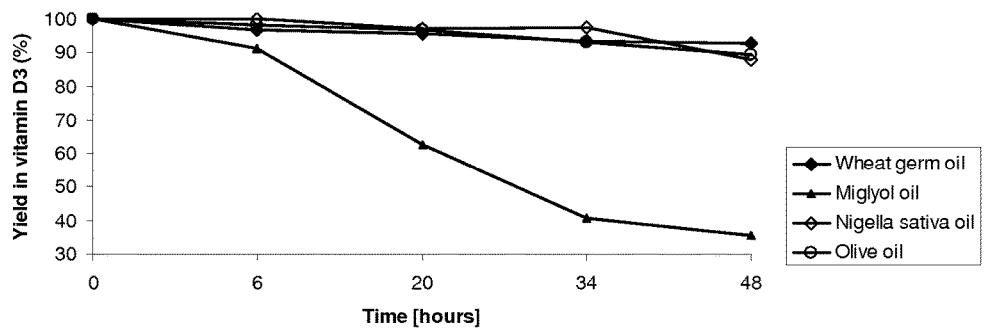
FIG. 6 represents the oxidative stability of vitamin $D_3$ dissolved in various hydrophobic stabilizer.

Other oil can be selected as hydrophobic stabilizer in view of their antioxidant content. Accelerated aging test of vitamin $D_3$ in presence of four different oils were performed. The stability over oxidation of vitamin $D_3$ in wheat germ oil, *Nigella sativa* oil, olive oil, or miglyol oil was compared. The degree of polyphenols in wheat germ oil, *Nigella sativa* oil, and olive oil was at least 13 mg of gallic acid per kg of oil, at least 230 mg of gallic acid per kg of oil, at least 120 mg of gallic acid per kg of oil respectively. Testing was performed by bubbling oxygen at a rate of 11 per minute in a solution containing vitamin $D_3$ and oil to be evaluated. Sampling was performed after 6, 20, 34 and 48 hours and data are represented in FIG. 6. The stability of vitamin $D_3$ was excellent in wheat germ oil (black rhomb), *Nigella sativa* oil (white rhomb) and olive oil (circular), while it was low in miglyol (black triangle). Without to be bound by the theory, it is suggested that the antioxidant content of the hydrophobic stabilizer can further improve the stability of the active component within the composition. Hence, in the present invention, the hydrophobic stabilizer may be an oil having an antioxidant content expresses as a degree in polyphenols therein higher than 1 mg of gallic acid per kg of oil. Preferably, oils having a degree in polyphenols higher than 10 mg of gallic acid per kg of oil, for example wheat germ oil, olive oil or *Nigella sativa* oil, may be suitable for the present invention.

According to the present invention, the carrier, i.e. calcium phosphate having a solubility in water lower than 0.1 wt %, allows stabilizing at least one active component in presence of a hydrophobic stabilizer. In addition, the stability of said at least one active component can be further enhanced by selecting a hydrophobic stabilizer having a defined antioxidant content or unsaturated fatty acids content. The hydrophobic stabilizer and/or the first carrier according to the invention can prevent oxidation of the active component.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application.

The invention claimed is:

1. A stable solid composition comprising a first carrier and an adsorbate adsorbed thereon, the adsorbate comprising at least one active component and a hydrophobic stabilizer thereof, wherein the carrier is a calcium phosphate, or derivatives thereof, having a solubility in water lower than 0.1 wt % at room temperature, and the at least one active component is soluble in the hydrophobic stabilizer, wherein the hydrophobic stabilizer comprises one or more $C_{3-22}$ fatty acids or ester or glyceride derivatives thereof, or mixture thereof.

2. The composition according to claim 1 wherein the calcium phosphate has Ca/P molar ratio ranging from 0.95 to 2.0.

3. The composition according to claim 1 wherein the calcium phosphate has a water content lower than 3.0%.

4. The composition according to claim 1 wherein a weight ratio between the first carrier and the adsorbate ranges from 200:1 to 2:1.

5. The composition according to claim 1 wherein a weight ratio between the at least one active component and the at least one hydrophobic stabilizer in the adsorbate ranges from 1:2 to 1:100.

6. The composition according to claim 1 wherein the hydrophobic stabilizer is an oil and the active component is oil-soluble.

7. The composition according to claim 1 wherein the at least one active component is selected from the group consisting of vitamins, perfume oils, flavours, carotenoids, xanthophylls, antioxidants, unsaturated fatty acids, oil-soluble enzymes and oil-soluble proteins.

8. The composition according to claim 1 wherein the at least one active component comprises a vitamin D derivative.

9. The composition according to claim 1 wherein the hydrophobic stabilizer has an antioxidant content expressed as degree of polyphenols in the hydrophobic stabilizer of at least 1 mg gallic acid per kg of hydrophobic stabilizer.

10. The composition according to claim 1 wherein the hydrophobic stabilizer is an oil containing at least 55 wt % of unsaturated fatty acids or ester or glyceride derivatives thereof.

11. A method for preparation of a stable solid composition, the method comprising:
    dispersing at least one active component into a hydrophobic stabilizer to form an adsorbate,
    contacting said adsorbate with a first carrier, and adsorbing the adsorbate onto the first carrier to form a composition,
    homogenising the composition obtained in the previous step, to form a stable solid composition,
    wherein the first carrier is a calcium phosphate, or derivatives thereof, having a solubility in water lower than 0.1 wt % at room temperature,
    wherein the hydrophobic stabilizer comprises one or more $C_{3-22}$ fatty acids or ester or glyceride derivatives thereof, or mixture thereof.

12. A method comprising:
    providing a human or animal food composition having a food ingredient, wherein the food ingredient is the stable solid composition according to claim 1.

13. An animal or human food composition comprising the composition according to claim 1.

14. A pharmaceutical preparation comprising the composition according to claim 1.

15. The composition according to claim 1, wherein the at least one active component comprises vitamin $D_3$.

16. The composition according to claim 1, wherein the first carrier is tricalcium phosphate.

* * * * *